(12) United States Patent
Cruz et al.

(10) Patent No.: US 8,520,193 B2
(45) Date of Patent: Aug. 27, 2013

(54) RAPID IRRADIATION TEST FOR GRANULATES

(75) Inventors: Marisa Cruz, Grokrotzenburg (DE); Rainer Fuchs, Moembris (DE); Frank Dieter Kuhn, Gelnhausen (DE)

(73) Assignee: EVONIK DEGUSSA GmbH, Essen (DE)

( * ) Notice: Subject to any disclaimer, the term of this patent is extended or adjusted under 35 U.S.C. 154(b) by 111 days.

(21) Appl. No.: 13/141,915

(22) PCT Filed: Dec. 29, 2009

(86) PCT No.: PCT/EP2009/067976
§ 371 (c)(1),
(2), (4) Date: Jun. 23, 2011

(87) PCT Pub. No.: WO2010/081630
PCT Pub. Date: Jul. 22, 2010

(65) Prior Publication Data
US 2011/0260078 A1    Oct. 27, 2011

(30) Foreign Application Priority Data
Jan. 13, 2009  (DE) .......................... 10 2009 000 177

(51) Int. Cl.
*G01N 1/00* (2006.01)
*G01N 21/84* (2006.01)
*G01B 1/00* (2006.01)

(52) U.S. Cl.
CPC . *G01B 1/00* (2013.01); *G01N 21/84* (2013.01)
USPC .............................................. 356/36; 356/426

(58) Field of Classification Search
CPC .................................. G01N 1/00; G01N 21/84
USPC ....................... 356/334–342, 36–38, 426–428
See application file for complete search history.

(56) References Cited

U.S. PATENT DOCUMENTS 3,982,420 A * 9/1976 Blevins et al. ................. 374/17
4,101,644 A * 7/1978 Frosch et al. ................. 423/581
5,953,129 A * 9/1999 Anderlik et al. .............. 356/402

(Continued)

FOREIGN PATENT DOCUMENTS

| CN | 101248112 A | 8/2008 |
| DE | 28 16 548 | 10/1979 |
| DE | 30 47 370 | 7/1982 |
| DE | 198 39 669 C1 | 8/2000 |
| EP | 1 947 444 | 7/2008 |
| WO | 00 13000 | 3/2000 |

OTHER PUBLICATIONS

International Search Report issued Mar. 29, 2010 in PCT/EP09/067976 filed Dec. 29, 2009.

(Continued)

*Primary Examiner* — Michael P Stafira
(74) *Attorney, Agent, or Firm* — Oblon, Spivak, McClelland, Maier & Neustadt, L.L.P.

(57) ABSTRACT

Method for irradiating granules, in the case of which the granules are arranged in a sample container (2) and are irradiated with an irradiation lamp (3), the granules being periodically mixed during the irradiation such that different surfaces of the granules are irradiated.
It is preferred to make use for the irradiation of a device which comprises
a. at least one irradiation lamp (3), and
b. at least one sample container (2) for the granules to be irradiated,
the sample container being connected to a drive so that the sample container can be moved during the irradiation and the granules can be mixed.

18 Claims, 1 Drawing Sheet

(56) References Cited

U.S. PATENT DOCUMENTS

| | | | |
|---|---|---|---|
| 5,992,245 A * | 11/1999 | Takei et al. | 73/865.5 |
| 6,433,343 B1 * | 8/2002 | Cimino et al. | 250/455.11 |
| 7,256,889 B2 * | 8/2007 | Bruins | 356/326 |
| 7,345,114 B2 * | 3/2008 | Yoshimi et al. | 525/331.5 |
| 2001/0037980 A1 * | 11/2001 | Yamamoto et al. | 210/748 |
| 2007/0173611 A1 * | 7/2007 | Yoshimi et al. | 525/331.5 |
| 2008/0169428 A1 | 7/2008 | Schoenlein | |
| 2009/0321682 A1 * | 12/2009 | Kajikawa et al. | 252/194 |
| 2011/0054080 A1 | 3/2011 | Berlineanu et al. | |

OTHER PUBLICATIONS

U.S. Appl. No. 13/140,911, filed Jun. 20, 2011, Cruz, et al.
U.S. Appl. No. 13/144,418, filed Jul. 13, 2011, Cruz, et al.
U.S. Appl. No. 13/144,365, filed Sep. 1, 2011, Berlineanu, et al.
Combined Chinese Office Action and Search Report issued Nov. 15, 2012 in Chinese Patent Application No. 200980154284.7 (with English-language translation).

* cited by examiner

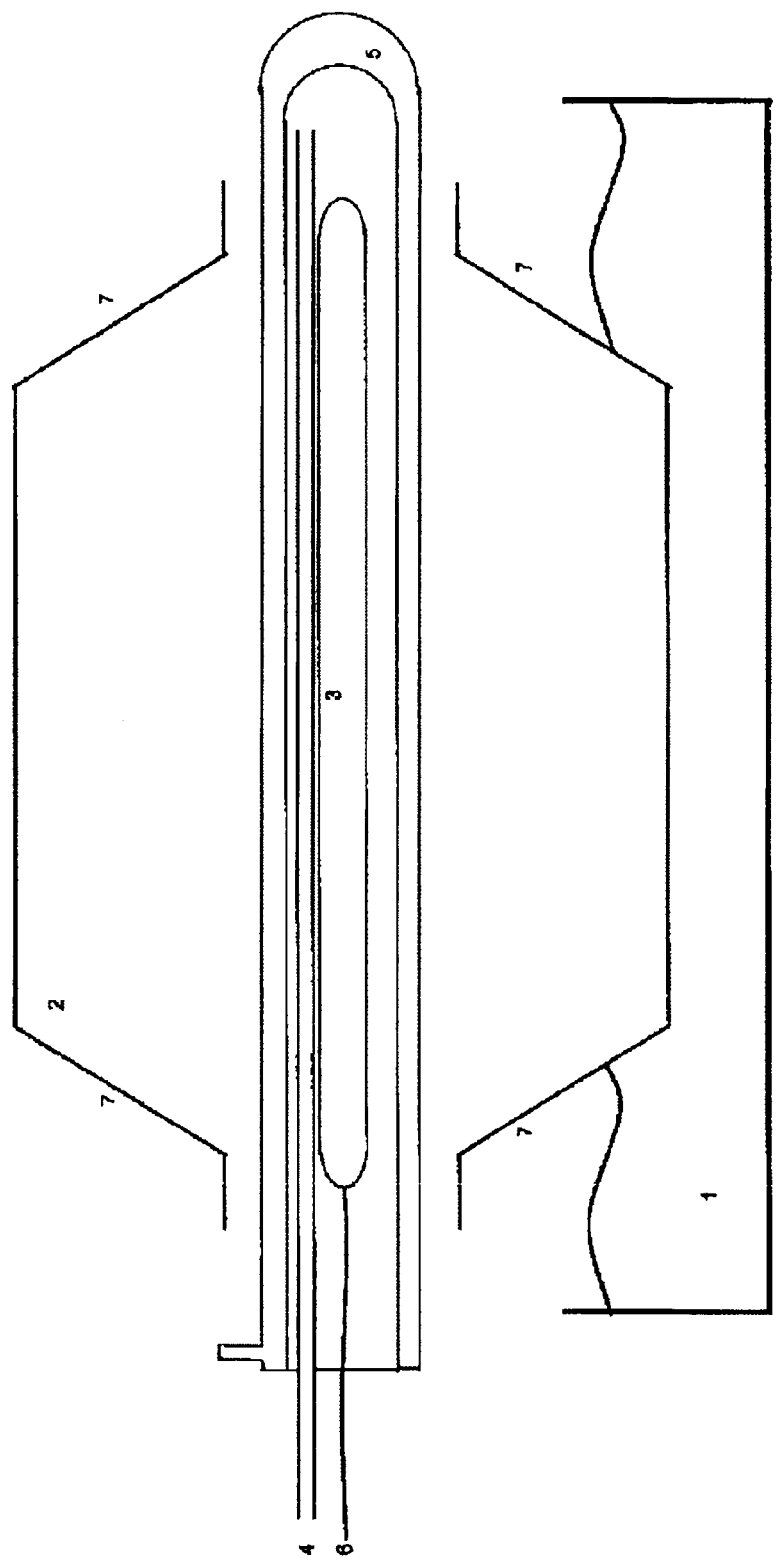

RAPID IRRADIATION TEST FOR GRANULATES

FIELD OF THE INVENTION

The present invention relates to a fast irradiation test for granules, preferably inorganic or organic granules, with particular preference plastic granules, and to a device for such a test.

PRIOR ART

Plastic granules are a typical supply form of thermoplastics from the base material manufacturers for the plastic processing industry. Because of their free-flowing capability, they are a bulk material, such as sand or gravel, and therefore can be transported and further processed comparatively easily.

There has recently been intensive discussion of the use of plastic granules as filling material for artificial lawns. For example, European Patent Application EP 1 416 009 A1 discloses the use of coated rubber particles as bedding material or as a loose elastic layer for artificial lawns or other floor coverings. The rubber particles are primarily of irregular n-polygon shape, and preferably have a mean size of between 0.4 mm and 2.5 mm up to a maximum of 4.0 mm. The individual rubber particles are provided over their complete surface with a 5 μm to 35 μm thick coat. The coat forms a permanently elastic coating which is intended largely to prevent pollutants, such as zinc, from being washed out. Furthermore, the aim is for this encapsulation to reduce a rubber smell typical of old rubber.

However, it is important for the application as filling material for artificial lawns to learn how the properties of such plastic granules change with time and insolation (so called ageing of the plastic granules). However, there is no test known to date which can be used in a simple way to quickly and cost-effectively simulate and estimate the insolation of plastic granules, and which enables the effect of the irradiation on the plastic granules, in particular of particle surfaces, to be determined within a short time.

All that are known are various treatment methods for irradiating surfaces of coated or uncoated sheeting or other two-dimensional surfaces, or coated or uncoated particles. For example, in testing the effect of UV rays on automobile paints use is frequently made of the Sun Test which can, moreover, also be used for particulate systems. In this case, a container is applied into which the coated or uncoated particles which are to be exposed are scattered and then exposed.

As a further example for the irradiation of coated or uncoated particles, Institut ISA Sport evaluates the weathering resistance of filling materials for artificial lawns by using an appliance which operates according to Standard ISO 4892-3. In this case, coated or uncoated rubber granules are subjected to climatic simulation in which the sample is stressed with UV light for a time period of 125 days.

However, these tests have various disadvantages which impede a fast estimation of the influence of insolation on the properties of plastic granules:

The tests are protracted and exceptionally time intensive, since they generally require an irradiation of several months or years.

There is presently no test which permits coated or uncoated particles, such as plastic granules for example, to be stressed uniformly over the entire surface with exposure and weathering. However, this is necessary in order to achieve as uniform as possible a behaviour of all the coated or uncoated particles over their entire surface. The exposure of only one side of the coated or uncoated granules results in two greatly different surfaces, for which reason diverse further reaching analyses and determinations (for example pollutant elution, colour measurement) at the exposed coated or uncoated granules are possible only with great difficulty.

Some of the prior tests can treat only a little material at one time; however it is important for there to be sufficient specimen material available in order to carry out methods of analysis subsequent to the irradiation (for example colour measurement, pollutant elution).

It is sometimes necessary to irradiate surfaces while they are suspended (for example in the Xenon test). This can be performed with granules only when the latter are bonded onto a surface which is then irradiated while suspended. In this case, the detachment of the particles is extremely expensive, and the adhesive remaining on the particles corrupts the results of subsequent examinations. Moreover, again only one particle side is irradiated.

ABSTRACT OF THE INVENTION

It was therefore an object of the present invention to indicate possibilities for better simulation of the influence of insulation on the properties of granules, in particular of filling materials for artificial lawns.

It would be greatly advantageous in developing coatings of particles to obtain as quickly as possible results which can be used for the purposes of testing various coatings for their stability in relation to UV irradiation, and of selecting the better coatings.

It would be very particularly advantageous if it were possible to apply the UV radiation which strikes the Earth, that is to say UV-B and UV-A radiation with a wavelength>295 nm, in general. It would, moreover, be particularly advantageous if UV-B radiation could chiefly be utilized for the testing, the point being that very many instances of damage to coatings result from stress by UV-B radiation.

Furthermore, a search was also made for a possibility of achieving a possibly uniform effect on the entire surface of the granules.

In particular, the aim was a solution which
  permits a fast simulation of the influence of insulation on the properties of granules,
  can be easily implemented and handled,
  can be realized as cost-effectively as possible,
  can be applied as universally as possible,
  requires as few minimum specimen amounts as possible, but nevertheless can provide sufficient specimen amounts of exposed granules for subsequent examinations,
  if appropriate, however, also enables the treatment of large specimen amounts,
  is as selective as possible in order to permit distinction of the ageing behaviour even in the case of very similar granules, and
  enables not only the measurement of a point, but also the measurement of a profile of the ageing over time; it is thereby possible to obtain further important indications relating to the ageing behaviour of coatings, particles and, in particular, rubber granules of old tyres. Furthermore, it would also thus be possible to determine how the type and amount of a pigmentation including the granules could influence the ageing.

This and further objects which follow from the contexts discussed are achieved by provision of a method for irradiating granules which has all the features of the independent method claim. Particularly expedient variants of the method are described in the subclaims referring back thereto. A device which is particularly suitable for carrying out the inventive method is also claimed.

Owing to the fact that the granules are arranged in a sample container and irradiated with an irradiation lamp, the granules being periodically mixed during the irradiation such that different surfaces of the granules are irradiated, it is possible in a way not immediately predictable to more effectively simulate the influence of insulation on the properties of granules, in particular of filling materials for artificial lawns.

The inventive mode of procedure also results, moreover, in numerous further advantages:
- The inventive method permits the examination both of coated and of uncoated particles, and also examination of coated or uncoated particle mixtures.
- The inventive method is exceptionally fast and very easy to carry out, and has only a very low requirement in terms of labour and time. In particular, it enables conclusions relating to possibly occurring long term UV damage as a consequence of insulation of the irradiated coated or uncoated product through the use of a high dose of radiation during a short irradiation period.
- The inventive method is very cost-effective.
- The inventive method is very flexible with reference to the sample amount to be examined. It is possible to obtain both large amounts and also small amounts of aged granules, depending on how much sample material is required for the subsequent examinations.
- It is possible to test without prior fixing of the granules.
- In the case of the inventive method, the entire surface of the granules is uniformly stressed, the result being a substantially simpler determination of the properties of the aged granules.
- The application of the inventive method also renders it possible to examine granules of complex structure which are, for example, irregularly coated, and/or have an angular shape or another more complex, if appropriate irregular or spherical, shape.

DRAWING

The drawing of FIG. 1 shows a preferred embodiment of a device for irradiating granules.

LIST OF REFERENCE NUMERALS

| | |
|---|---|
| 1 | Temperature control element |
| 2 | Sample container |
| 3 | Irradiation lamp |
| 4 | Inert gas purge |
| 5 | Quenching space |
| 7 | Bevelled ends |

DETAILED DESCRIPTION OF THE INVENTION

In the case of the inventive method for irradiating granules, expediently inorganic or organic granules, preferably plastic granules, with particular preference coated plastic granules, the granules are arranged in a sample container and are irradiated with an irradiation lamp, the granules being periodically mixed during the irradiation such that different surfaces of the granules are irradiated.

The term "periodically" denotes in this context an activity (here, the mixing) regularly recurring at equal intervals, preference being given in the present case to a repetition of at least 2 operations, preferably at least 5 operations, with particular preference at least 10 operations.

The rate of repetition of the activity (here, the mixing) is preferably at least 1 operation per minute, preferably at least 5 operations per minute, with particular preference at least 10 operations per minute. A continuous mixing is performed during the irradiation in the context of a particularly preferred embodiment of the present invention.

Within the scope of the present invention, the term "mixing" denotes a thorough mixing of the granules. This preferably leads to a variation in the three-dimensional orientation of at least two granules, preferably of at least 5 granules, with particular preference of at least 10 granules. Furthermore, the positions of at least two granules, preferably of at least 5 granules, with particular preference of at least 10 granules, relative to one another are preferably varied.

In the context of a particularly preferred embodiment of the present invention, the granules are mixed in such a way that at least two different, preferably at least three different, surfaces of the granules are consecutively irradiated, each of these surfaces being irradiated at least twice, preferably at least five times, in particular preferably at least 10 times.

The inventive irradiation method differs on the basis of the periodic mixing of the granules during the irradiation from the known irradiation methods, in the case of which the granules are not mixed during the irradiation, and only one surface of the granules is continuously irradiated.

The inventive method leads to a very uniform irradiation of the overall surface of the granules. The irradiation is preferably performed in such a way that the difference between the shortest irradiation time of a surface of the granules and the longest irradiation time of a surface of the granules is at most 100%, preferably at most 50%, in particular at most 20%, of the longest irradiation time of a surface of the granules.

The irradiation simulates the influence of light, in particular of sunlight, on the granules. The light therefore preferably comprises components of natural sunlight; the irradiation is preferably performed with a wavelength in the range from 1 nm to 1000 nm, preferably with a wavelength in the range from 200 nm to 400 nm (so-called near UV radiation), with particular preference with a wavelength in the range from 295 nm to 315 nm (so-called UV-B radiation).

It is particularly advantageous for the purposes of the present invention to use an inventive device for irradiating granules. This device comprises
a. at least one irradiation lamp, and
b. at least one sample container for the granules to be irradiated, the sample container being connected to a drive so that the sample container can be moved during the irradiation and the granules can be mixed.

The position of the irradiation lamp relative to the sample container can be freely selected in principle, the irradiation lamp preferably being arranged inside the sample container. However, it can also be arranged outside the sample container, although this variant is less preferable.

Preference is conferred, furthermore, on a direct effect of the beams on the granules to be irradiated. Materials which can partially or completely absorb or deflect the light of the irradiation source are therefore to be avoided if possible on the straight line connection between the irradiation lamp and the granules, unless special materials such as, for example, filters are used to achieve a desired reduction in undesired radiation such as, for example, IR radiation (thermal radiation) in conjunction with the best possible transparency to UV-B radiation, in particular.

The irradiation lamp is preferably enclosed in an inert gas purge which is preferably arranged between the irradiation lamp and the sample container. Inert gases particularly suitable for the purposes of the present invention comprise, in particular, nitrogen and all noble gases such as helium and neon.

Within the context of a particularly preferred embodiment of the present invention, it is provided, furthermore, to purge the granules in the sample space with at least one gas and/or at least one liquid, in order to examine the influence of the gas and/or the liquids on the properties of the granules during the irradiation. Particularly suitable for these purposes are air, steam, acid steam, acid rain and water.

Furthermore, the irradiation lamp is preferably provided with a filter which filters out IR radiation (780 nm to 1 mm) at least partially from the radiation spectrum of the irradiation lamp. The irradiation lamp is preferably enclosed to this end in a quenching space which comprises an IR quenching liquid and is preferably arranged between the irradiation lamp and the sample container, with particular preference between the inert gas purge and the sample container.

For the purposes of the present invention, particularly suitable IR quenching liquids comprise all fluids which are liquid under the examination conditions and which at least partially absorb light in the range from 780 nm to 1 mm.

Heating of the granules during irradiation is largely avoided by the use of an IR filter.

The shape of the sample container is likewise not subject to any particular restrictions. However, sample containers with a region which comprises a straight cylindrical shape have proved themselves in particular, the irradiation lamp preferably being arranged centred in the middle of the cylinder.

In the context of a particularly preferred embodiment of the present invention, the irradiation lamp has an elongated shape, the alignment of the irradiation lamp preferably corresponding to the main axis of the sample container, in particular the main axis of a straight cylindrical part of the sample container.

The inner walls of the sample container preferably comprise a reflecting material, the purpose of which is to guide to the granules after reflection the light which, for example, has not struck, or has passed by, the granules. The effectiveness of the irradiation can be substantially increased in this way. Reflecting materials particularly suitable in this context lead to a reflection of at least 5%, preferably at least 25%, with particular preference at least 50%, of the incident radiation. Steel is a very particularly suitable material for this purpose.

At least 80% of the entire inner surface of the sample container is preferably coated with the reflective material and/or consists thereof.

In the context of a particularly preferred embodiment of the present invention, the sample container further comprises a material with a high thermal conductivity, preferably a thermal conductivity of greater than 1 W/(m·K), in particular greater than 3 W/(m·K), measured at 25° C.

At least 80% of the sample container preferably consists of a material with a high thermal conductivity.

In addition, the device of the present invention preferably comprises at least one temperature control element, preferably a heating or cooling element, in particular a cooling element which permits the irradiation of the plastic particles under permanently prescribed temperature conditions, or in permanently prescribed temperature ranges.

The sample container furthermore preferably comprises at least one mixing element for mixing the granules during the irradiation. Flow disruptors which at least partially deflect the movement of the granules along the main axis of the container as the latter is rotating have particularly proved suitable in this context.

In order to increase the mixing effect of the granules, the head and/or the foot end, particularly preferably the head and the foot end, of the sample container is/are bevelled in order to mix the granules even more intensively during the irradiation. In this case, the inside diameter of the sample container preferably decreases in the direction of the bevelled end.

The size of the sample container is of subordinate importance. The sample container is preferably dimensioned in such a way that it can hold between 10 g and 500 kg of granules. Sample containers very particularly suitable for the purposes of the present invention have a capacity in the range from 1 kg to 10 kg.

During the irradiation, the sample container is filled with granules, preferably to 0.1% to 10%, preferably to 0.5% to 5%, with reference to the total volume of the sample container.

Within the scope of the present invention, the sample container is preferably rotated in order to achieve the mixing of the granules. In this case, the rotation is preferably about a main axis of the container, the irradiation lamp preferably likewise being positioned along this main axis.

The rate of rotation is preferably in the range from 1 RPM to 500 RPM.

The design of an irradiation apparatus particularly suitable for the purposes of the present invention is shown diagrammatically in FIG. 1. It comprises an irradiation lamp (3) and a sample container (2), the irradiation lamp (3) being of elongated design and arranged in a fashion centred along the main axis of the sample container (2).

The sample container (2) has a straight cylindrical shape with bevelled head and foot ends (7), the inside diameter of the sample container (2) decreasing in the direction of the bevelled ends (7).

The sample container (2) is preferably fabricated from a thermally conductive steel which reflects at least 5% of the incident radiation.

The irradiation lamp is enclosed in an inert gas purge (4) which is arranged between the irradiation lamp (3) and the sample container (2).

Furthermore, the irradiation lamp (3) is enclosed in a quenching space (5) which contains an IR quenching liquid and is arranged between the inert gas purge (4) and the sample container (2).

The device comprises a temperature control element (1), preferably a refrigerating waterbath, for controlling the temperature of the sample container (2) in the course of the irradiation.

During the irradiation, the sample container (2) is rotated, preferably continuously, by means of the drive about the main axis of the sample container (2) along which the irradiation lamp (3) is positioned.

The temperature during the irradiation can be freely selected in principle and, in particular, be tuned to the conditions which are to be simulated or adjusted. For the purposes of the present invention, the temperature is, however, preferably in the range from 0° C. to 95° C.

The intensity of the irradiation of the granules can be controlled via the time period of the irradiation and via the irradiance. The irradiation is preferably performed for a time in the range from 1 h to 1000 h, in particular in the range from 24 h to 500 h.

Furthermore, the irradiation of the granules is preferably performed with an irradiance in the UV-B region in the range from 1 W/m$^2$ to 10 000 W/m$^2$, in particular in the range from 100 W/m$^2$ to 1000 W/m$^2$.

The inventive fast irradiation method and the inventive device for irradiating granules are suitable in principle for irradiating all types of granules. However, it is particularly preferred to use them for the irradiation of coated plastic granules, in particular of coated rubber particles, which are utilized as bedding material or as a loose elastic layer for artificial lawns or other floor coverings.

The rubber particles are generally of irregular n-polygon shape and preferably have a mean size of between 0.4 mm and 4.0 mm. The maximum particle size of the particles is preferably less than 10 mm, with particular preference less than 7 mm. The minimum particle size of the particles is preferably greater than 0.1 mm, with particular preference greater than 0.2 mm. The individual rubber particles are preferably provided with a 5 µm to 35 µm thick coat. The coat preferably forms a permanently elastic coating which is intended largely to prevent pollutants such as, for example, zinc from being washed out. Moreover, this encapsulation is intended to reduce a rubber smell typical of old rubber. Further details relating to such plastic granules can be taken, for example, from European Patent Application EP 1 416 009 A1.

Furthermore, the inventive method can also be used to study the influence of insulation on the bonding of a composite material. For this purpose, it is preferred to examine particles which have been obtained from the composite material, and which have preferably been cut, punched or broken from the composite material.

The invention is further explained below by means of a plurality of examples, without the aim of thereby limiting the idea of the invention.

EXAMPLES

A device having a schematic design in accordance with FIG. 1 was used for the irradiation. In a cylindrical VA drum reactor with a volume of approximately 12 litres (length: 19.6 cm; diameter: 27.4 cm; irradiated area: 1687 cm$^2$) with flow disruptors and water cooling, a borosilicate glass tube with water cooling and nitrogen purge was positioned in the rotation axis, and an iron-doped medium-pressure Hg lamp with a 150 mm luminous length of 1.8 kW maximum output was positioned in the borosilicate glass tube, said lamp being capable of operation by a suitable electronic ballast.

100 g of the coated or uncoated sample to be irradiated was weighed in a beaker and filled into the reactor. Thereafter, the immersion tube with the UV lamp was installed in the holder, provided for the purpose, of the plant. The nitrogen flow was set to 6 L/h, while the cooling water flow was set to 100 L/h. The UV loading system was then switched on and the motor, which ensured reactor rotation (12 RPM), was started.

The coated or uncoated sample to be examined was now irradiated at 1.55 kW lamp output (wavelength of the radiation loading the sample being in the UV region of 295-380 nm) for 240 hours under rotation.

After termination of the irradiation, the system was switched off and the irradiated coated or uncoated sample was removed quantitatively from the reactor.

The sample was subjected to subsequent tests in order to examine the effect of the UV irradiation.

The intensity of the described UV test in the UVB region was approximately 360 times more intense than the natural sunlight at noon in summer in Germany through 24 hours of permanent irradiation. The following powers went to the UVA and UVB regions in conjunction with a lamp output of 1.55 kW:

UVB(295-315 nm)=74 W

UVA(315-380 nm)=325 W;

The drum dimensions gave an irradiated area of 1687 cm$^2$, signifying an irradiance of 439 W/m$^2$ for the UVB region.

The procedure in obtaining the results was as follows:

Firstly, the colour, the abrasion or a zinc elution of the non-irradiated product were measured. A specimen of a product was then respectively subjected to the UV irradiation in the UV irradiation apparatus, the irradiated product was removed from the apparatus as quantitatively as possible, and respectively subjected to a further test or all the tests: either zinc elution, or measurement or abrasion or all specified tests.

The difference of the [values of the examination after UV irradiation] minus [grounds of the examination before UV irradiation] yields a delta value whose level and sign describe the effects of the UV irradiation on the tested material.

UV-Elutable Substances Such as, for Example Zn

| Designation | Untreated specimen Zinc (mg/L) | After UV Zinc (mg/L) | $\Delta_{Zn\ (mg/L)}$ |
|---|---|---|---|
| GTR | 5.0 | 5.4 | 0.4 |
| Granufill (CGTR) | 3.6 | 5.4 | 1.8 |
| Evonik 1 | 0.3 | 1.3 | 1.0 |
| Evonik 2 | 0.8 | 2.6 | 1.8 |
| Evonik 3 | 0.5 | 2.4 | 1.9 |

The zinc content was determined in accordance with Prestandard DIN V 18035-7, 6.11.3 (sports fields, part 7: artificial lawn surfaces).
GTR: ground tyre rubber, fine rubber granules from the Genan Gruppen GmbH company UV-Abrasion

| Designation | Untreated specimen Abrasion (%) | After UV Abrasion (%) | $\Delta_{abrasion}$ |
|---|---|---|---|
| RTW GO 2008 RAL 6025 (CGTR) | 6.0 | 7.37 | 1.37 |
| Granufill (CGTR) | 2.84 | 2.51 | −0.33 |
| GTR | 1.25 | 1.6 | 0.35 |
| Evonik 1 | 1.50 | 1.80 | 0.30 |
| Evonik 2 | 1.40 | 1.90 | 0.50 |
| Evonik 3 | 1.10 | 2.50 | 1.40 |

CGTR: coated GTR

UV-Ink

|  | Untreated specimen | | | After UV | | | |
| --- | --- | --- | --- | --- | --- | --- | --- |
| Designation | L | a | B | L | a | b | ΔE*ab |
| MRH-grün SOCC (CGTR) | 18.95 | −8.68 | 8.07 | 14.81 | −6.01 | 8.24 | 4.93 |
| RTW GO 2008 RAL 6025 (CGTR) | 29.90 | −7.88 | 14.18 | 22.19 | −4.36 | 8.78 | 10.06 |
| Granufill (CGTR) | 18.20 | −12.79 | 9.80 | 15.74 | −7.54 | 7.37 | 6.29 |
| Evonik 1 | 36.96 | −5.31 | 2.25 | 36.00 | −3.66 | 2.03 | 1.92 |
| Evonik 2 | 40.88 | −7.22 | 6.70 | 39.42 | −5.40 | 5.82 | 2.49 |
| Evonik 3 | 38.26 | −6.08 | 3.55 | 36.26 | −3.48 | 2.59 | 3.42 |

The colour measurement was determined along the lines of DIN 5033.

The invention claimed is:

1. A device, comprising:
   a. at least one irradiation lamp; and
   b. at least one sample container suitable for granules to be irradiated,
   wherein the sample container is connected to a drive so that the sample container can be moved during the irradiation and the granules can be mixed, and
   wherein the device is suitable for irradiating at least one granule
   wherein the irradiation lamp is arranged inside the sample container.

2. The device of claim 1, wherein the sample container comprises a region of a straight cylindrical shape, and the irradiation lamp is arranged centered in the middle of the cylinder.

3. The device of claim 1, wherein at least one inner wall of the sample container comprise a reflecting material.

4. The device of claim 1, wherein the sample container comprises a material with a thermal conductivity of greater than 1 W/(m·K), measured at 25° C.

5. The device of claim 4, further comprising:
   at least one temperature control element.

6. The device of claim 1, wherein the sample container comprises at least one mixing element suitable for mixing the granules during the irradiation.

7. The device of claim 1, wherein at least one selected from the group consisting of a head end and a foot end of the sample container is bevelled in order to mix the granules during the irradiation.

8. A method for irradiating at least one granule, the method comprising:
   periodically mixing granules during irradiation such that different parts of surfaces of the granules are irradiated,
   wherein the granules are arranged in a sample container and are irradiated with an irradiation lamp arranged inside said sample container; and
   wherein the granules are irradiated with a device, comprising:
   a. at least one irradiation lamp; and
   b. at least one sample container suitable for granules to be irradiated,
   wherein the sample container is connected to a drive so that the sample container can be moved during the irradiation and the granules can be mixed, and
   wherein the device is suitable for irradiating at least one granule.

9. The method of claim 8, wherein the granules are mixed in such a way that at least two different surfaces of the granules are consecutively irradiated, each of these surfaces being irradiated at least twice.

10. The method of claim 8 wherein the granules are irradiated with light with a wavelength in a range from 1 nm to 1000 nm.

11. The method of claim 8, wherein the sample container is rotated periodically with a rate in a range from 1 RPM to 500 RPM.

12. The method of claim 8, wherein the irradiation is carried out at a temperature in a range from 0° C. to 95° C.

13. The method of claim 8, wherein the irradiation is performed for a time in a range from 1 h to 1000 h.

14. The method of claim 8, wherein the irradiation is performed with light with an irradiance in a range from 1 W/m² to 10 000 W/m².

15. The method of claim 8, wherein coated rubber particles are present, and the coated rubber particles are irradiated.

16. The method of claim 8, wherein the granules are particles which have been obtained from a composite material.

17. The device of claim 2, wherein at least one inner wall of the sample container comprise a reflecting material.

18. The device of claim 2, wherein the sample container comprises a material with a thermal conductivity of greater than 1 W/(m·K), measured at 25° C.

* * * * *